United States Patent [19]

Schneider

[11] Patent Number: 4,924,716
[45] Date of Patent: May 15, 1990

[54] DISSOLUTION TESTING APPARATUS

[75] Inventor: Ortwin Schneider, Weiterstadt, Fed. Rep. of Germany

[73] Assignee: Erweka Apparatebau GmbH, Heusenstamm, Fed. Rep. of Germany

[21] Appl. No.: 352,277

[22] Filed: May 16, 1989

[30] Foreign Application Priority Data

May 19, 1988 [EP] European Pat. Off. ......... 88107995.8

[51] Int. Cl.⁵ .......................................... G01N 19/00
[52] U.S. Cl. ..................................................... 73/866
[58] Field of Search ................................. 73/866, 53

[56] References Cited

U.S. PATENT DOCUMENTS 3,802,272 4/1974 Bischoff et al. ...................... 73/866
4,754,657 7/1988 Schneider ............................. 73/866

FOREIGN PATENT DOCUMENTS 0278374 8/1988 European Pat. Off. ............. 73/866

Primary Examiner—Hezron E. Williams
Assistant Examiner—Joseph W. Roskos

[57] ABSTRACT

A dissolution testing apparatus which includes a rinsing stand, a test stand and a movable support member with a measuring vessel inclusive of an intake pipe and a filter. A filter stripping device is mounted to the support member by which the used filter can be replaced by a new filter.

13 Claims, 5 Drawing Sheets

DISSOLUTION TESTING APPARATUS

BACKGROUND OF THE INVENTION

The present invention relates to a dissolution testing apparatus with a rinsing stand at least one measuring ring vessel being reciprocable with respect to the rinsing stand and the test stand lifted position of the paddle and the rinsing paddle, wherein the means with on one hand one or several measuring vessel(s) and on the other hand rinsing stand and test stand are and suction pipe including a filter by means of which the liquid containing the substance to be examined with respect to the dissolution behaviour thereof can be extracted, the suction pipe therein being lifted and lowered relative to the measuring vessel.

The present invention in particular relates to a dissolution testing apparatus in which an exchange of filters between different measuring cycles is simplified and, in one preferred embodiment, is carried out entirely automatically.

A generic dissolution testing apparatus is generally available. Such dissolution testing apparatus serves for the investigation of the dissolution behaviour of a substance in a liquid and in particular for analyzing the dissolution behaviour of a medical tablet in a liquid, the composition of which essentially corresponds to that of gastric acid.

The know dissolution testing apparatus includes a rinsing stand, a test stand and a movable means carrying a plurality of measuring vessels in a water bath. The rinsing stand comprises a rinsing paddle for each measuring vessel, such paddle being driven with a rotary movement and being arranged as to permit lifting and lowering in a vertical direction. The test stand comprises a paddle for stirring the measuring liquid for each measuring vessel. All of the paddles can be driven in a rotary movement and can be lowered into the measuring vessels containing the substance to be examined as to the dissolution behaviour for stirring the liquid in the vessels. Furthermore, in this known dissolution testing apparatus a suction pipe is provided for each measuring vessel, such suction pipe together with corresponding paddle is submersible into the liquid containing the substance to be examined. The movable means, including the measuring vessels disposed in a water bath, can be driven in a horizontal direction to the position of the rinsing stand. In this position of the movable means, lowering of the rinsing paddles is effected for the purpose of rinsing the measuring vessels. Once the measuring vessels having been cleaned the rinsing paddles are lifted so that the movable means can be moved back to the position of the test stand. When this position is reached the paddles can be lowered into the measuring vessels for evenly stirring the liquid into which, at a given point of time, the substance to be examined is introduced. After a given period of stirring, the liquid is drawn off from the measuring vessels by means of the suction pipes. Such a cycle having been completed it will become necessary to exchange the filters located at the end portions of the suction pipes with new filters, which on one hand requires a good deal of expenditure of labor and on the other hand demands a staff having to be instructed and trained at least to a certain degree.

SUMMARY OF THE INVENTION

In accordance with the present invention a dissolution testing apparatus is provided such that the exchange of filters in the liquid measuring system is simplified. This object is accomplished by providing a dissolution testing apparatus having a rinsing stand comprising at least one rotatably drivable rinsing paddle capable of being lifted and lowered vertically relative to a measuring vessel, a test stand comprising at least one rotatably drivable test stand mixing paddle capable of being lifted and lowered vertically relative to the measuring vessel, with a movable support means comprising at least one measuring vessel, wherein by means of lowering a mixing paddle into a liquid containing a substance to be examined with respect to its dissolution behaviour the liquid can be stirred, the movable support means being reciprocable or movable between the rinsing stand and the test stand during the lifted position of the mixing paddle(s) and the rinsing paddle(s), wherein the movable support means with one or several measuring vessel(s) and the rinsing stand and test stand are shiftable with respect to one another. A suction pipe comprising a filter, by means of which suction pipe the liquid containing the substance to be examined can be extracted when the movable support means is in the position of the test stand, can be lifted and lowered together with the lifting and lowering of the rinsing paddle and/or the mixing paddle relative to the respective measuring vessel, wherein a filter stripping means is arranged at the movable support means, by means of which filter stripping means engages the filter in a first position of the movable support means.

The invention is based on the concept that the cyclic motion to be carried out by the movable means in the known dissolution testing apparatus in each measuring cycle can be made use of for simplifying or even completely automating the exchange of filters. A filter stripping means moving together with the movable support means is mounted at the support means, the filter capable of engaging the filter stripping means at a certain position of the movable support means.

According to the preferred embodiment of the present invention the filter stripping means is disposed such that, at first, upon a motion of the movable support means across a part of its path from the test stand to the rinsing stand in the first position, the filter can be engaged by the filter stripping means and during a subsequent lifting of the suction pipe, the filter can be stripped off from the suction pipe. In other words, the filter stripping means is arranged in such a manner that primarily upon the support means having been driven along part of its way from the test stand to the rinsing stand into the first position, the first filter can be engaged, thereupon a subsequent lifting of the suction pipe results in a removal of the filter from the suction pipe. In other words, an automatic stripping off of the filters from the suction pipes can be realized by merely utilizing the horizontal movement of the movable support means, as well as the vertical movement of the suction pipe, without a substantial degree of control technology and equipment being required for this purpose.

According to another preferred embodiment of the present invention, a filter loading means is arranged at the movable support means. The filter loading means carries a new filter, and the suction pipe is lowered into a second position upon a motion of the movable support means and in this lower position is connectable to a new filter by means of a clamp fit. The filter loading means carrying a new filter is disposed at the movable support means for achievement of a fully automated filter exchange, the suction pipe being lowerable into a second position after a motion of the movable support means having been carried out and in this lowered position being connectable to the new filter by means of clamp or gauge fit.

According to another preferred embodiment of the invention, the filter loading means comprises a rotary disc on which a plurality of new filters is arranged at uniform angular distances, and the rotary disk is turnable by the angular distance upon each deposition of a new filter on the suction pipe by means of a driving means. Since a plurality of filters are arranged at even angular distances on the rotary disk, which disk may be turned by a driving means by the angular distance each time a new filter is assembled on the suction pipe, a series of filter exchanges can be carried out entirely automatically, without a service person being required. A particularly simple way of effecting the further rotation of the rotary disk by even angular distances lies in that the driving means of the rotary disk is built as a stepping motor.

An extremely low demand in constructive expenditure for a filter loading means is achieved in an embodiment of the dissolution testing apparatus wherein at least two measuring vessels, two test stand paddles, two rinsing paddles and two suction pipes, each arranged beside another in a direction perpendicular to the direction of motion of the movable support means, are provided and the rotary disk serves as a common filter loading means for two adjacent suction pipes and is arranged such that the lowered suction pipes in the second position of the movable support means engages the filter stripping means, with two new filters being disposed on the common rotary disk.

The lowering and lifting of the suction pipes for the purpose of filter exchange can be effected in particulary simple manner in that the suction pipes together with the paddles are mounted on a bridge which may be lifted and lowered in a vertical direction.

Preferably a rinsing vessel into which the paddle can be submerged in the first position of the movable support means is disposed at the support means. For this reason, one single feed position of the movable means can be utilized for cleaning the paddles as well as for engaging the filters prior to removal.

BRIEF DESCRIPTION OF DRAWINGS

Preferred embodiments of the present invention will now be described with reference to the attached drawings, wherein.

DETAILED DESCRIPTION OF THE INVENTION

Figure 1:
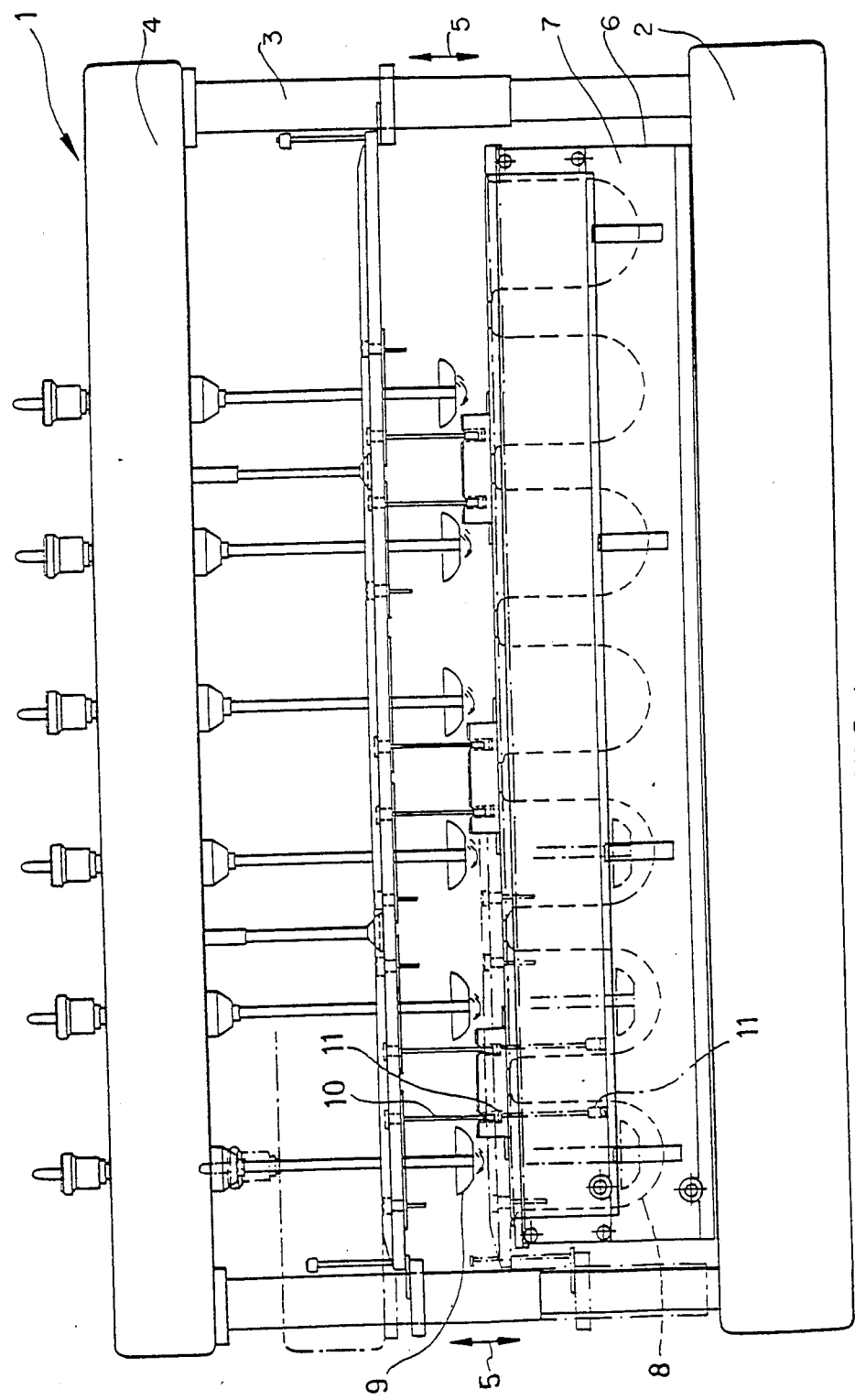
FIG. 1 is a front view of a first embodiment of a dissolution testing apparatus.

As can be seen from FIG. 1 a dissolution testing apparatus 1 includes a base part 2 in which driving units (not shown) are accomodated. A bridge 4 is arranged, movable in upward and downward directions, opposite to the base part 2 by means of columns 3. The vertical movement of the bridge 4 is indicated by arrows 5. A movable support means 6 is arranged above the base part 2, such means being reciprocatingly driven in a horizontal direction perpendicular to the plane of the drawing of FIG. 1. The movable support means 6 includes a water bath 7 serving as the steady and accurately fixed temperature regulator of the measuring vessels 8. The measuring vessels are intended for taking up a liquid in which a substance to be examined with respect to its dissolution behaviour is soluble. The relative motion between the support means 6 on the one hand and a test stand 13 and a rinsing stand 14 on the other may be effected by shifting the test stand and the rinsing stand with respect to the support means 6 which is stationary in the present case.

Paddles 9 are driven in a rotary direction by driving means (not shown) disposed within the bridge 4. Suction pipes 10, which carry at their lower ends filters 11, are connected to the bridge 4.

The bridge 4 and the paddles 9 disposed at the bridge 4, as well as the suction pipes 10 connected to the bridge via the columns 3, are shown in FIG. 1 in their upper vertical end position in full line and their lower vertical end position in dashed lines.

As can be seen, the paddles 9 in the lower vertical end position of the bridge 4, submerge into the measuring vessels 8. In this condition, the filters 11 are located at the ends of the suction pipes 10 in the lower portion of the measuring vessels 8.

Figure 2:
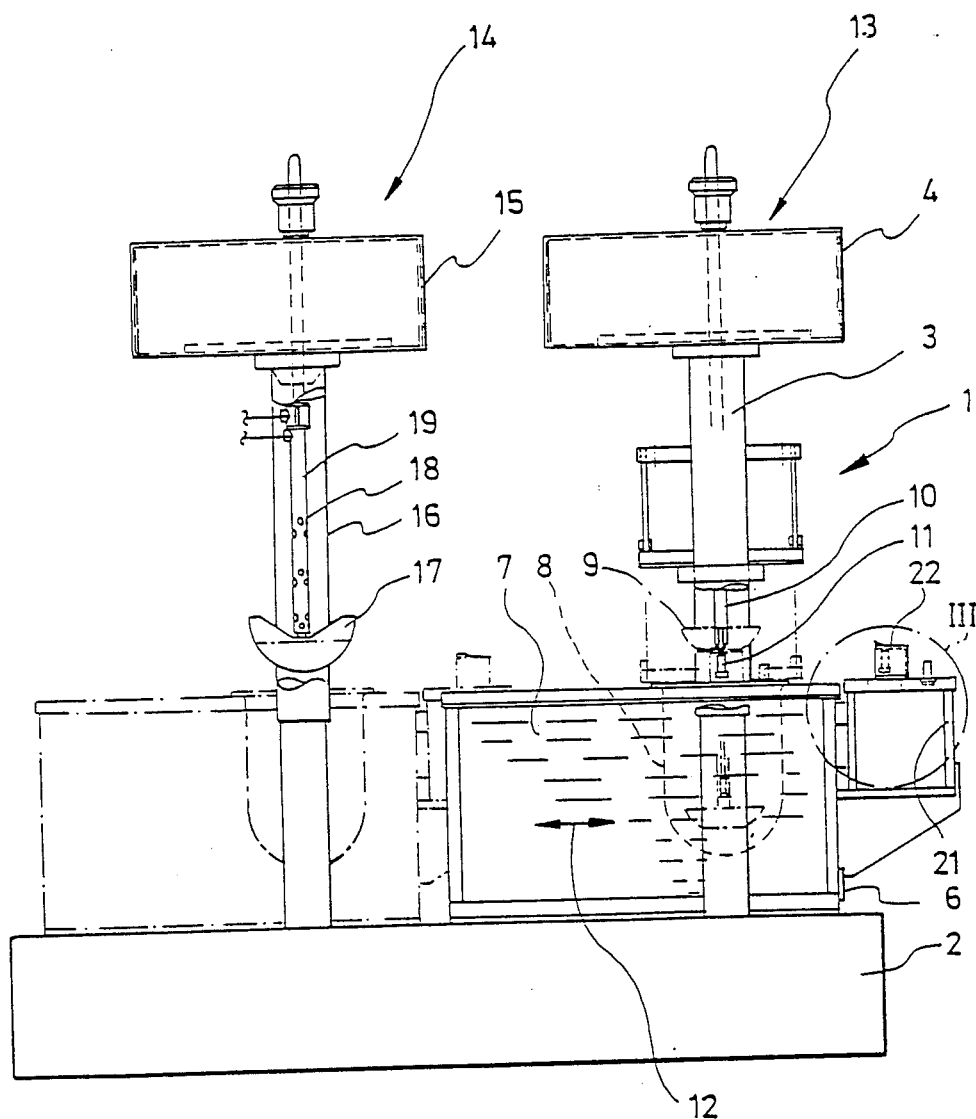
FIG. 2 is a side view of the first embodiment shown in FIG. 1.

FIG. 2 shows a side view, partly in cross-section, of the dissolution testing apparatus shown in FIG. 1. Reference numerals corresponding to those used in FIG. 1 relate to same parts.

The movable support means 6 can be moved in a reciprocating manner with respect to the base part 2 in the direction of the arrow 12. In the right-hand portion of the base part 2 a test stand is disposed, essentially being formed out of the columns 3, the bridge 4, the paddles 9 as the suction pipes 10 and shown in the side view in FIG. 1.

In the left-hand portion of the base part 2 a rinsing stand 14 is arranged, comprising a bridge 15 movable with respect to the base part 2 in a vertical direction via columns 16. Rinsing paddles 17 are rotatably supported at the bridge 15 of the rinsing stand 14. The rinsing paddles 17 are driven in rotary direction by a driving unit (not shown). The rinsing paddles 17 have a hollow shaft 19 comprising rinsing nozzles 18. A rinsing liquid may be fed to the hollow shaft and be sprayed out through the nozzles 18 for cleaning the measuring vessels 8 in the lowered position of the rinsing paddles 17, when the movable support means 6 is in the position shown in dash-dotted line on the left-hand side for rinsing the measuring vessels 8.

The movable support means 6 at its right-hand end (in FIG. 2) carries a rinsing vessel 21 into which the paddle 9 can be submerged in a first position of the movable support means 6. The first position of the movable support means 6 lies between the position shown in full lines, of the movable support means 6 in the site of the test stand and the position shown in dash-dotted lines, of the movable support means 6 in the site of the rinsing stand 14. In the first position, a fork-shaped filter stripping means 22 comes into engagement with the filter 11 at the lower end of the suction pipe 10, the suction pipe 10 together with the bridge 4 of the test stand 13 being in their vertically elevated position.

Figure 3:
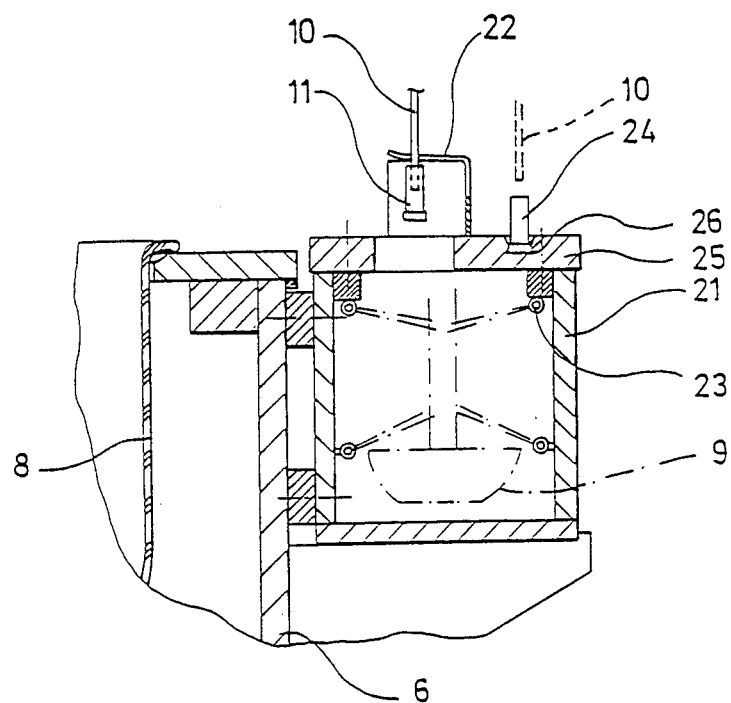
FIG. 3 shows a detail of FIG. 2, such detail being marked by means of dash-dotted circle and the reference number III.

The detail marked in FIG. 2 by means of the dash-dotted circle of the movable support means 6 is shown in enlarged view in FIG. 3. The horizontal position of the movable support means 6 which the latter has assumed in the view of FIG. 3 corresponds to the above-defined first position. As can be seen from FIG. 3, the fork-shaped filter stripping means 22 in this first position of the movable support means 6 overlaps the filter 11 at the end of the suction pipe 10 which, as has already been set forth, is in its at least partially elevated position in the vertical direction. A lifting of the bridge 4 and thus of the suction pipe 10 in this first position of the movable support means 6 results in a stripping off the filter 11 from the lower end of the suction pipe 10, whereupon the filter 11 falls down through an orifice, which can be seen better in FIGS. 4 and 5 to be explained later. Subsequently, the bridge 4 is lowered, whereby the paddle 9 is brought into the position shown in FIG. 3 in dash-dotted line, in which it is cleaned in the rinsing vessel 21, by means of cleansing nozzles 23, of residue of the liquid and the substance to be examined from the latest test cycle.

When the movable support means 6 is slightly moved furtheron in the direction of the rinsing stand (to the left-hand side in FIG. 3), the suction pipe 10 opposite the movable support means 6 reaches the position shown in dash-dotted line in FIG. 3, in which position the suction pipe 10 comes into a position above a new filter 24 held in a recess 26 of the cover 25 of the rinsing vessel 21. When the bridge 4 is lowered in this relative position of the suction pipe 10, such position being referred to as the second position, the end of the suction pipe 10 comes into mesh with the new filter 24 which is fixedly disposed on the suction pipe 10 in a clamp or gauge fit by simply slipping it over the pipe.

In the first embodiment discussed with reference to FIGS. 1 to 3 of the dissolution testing apparatus according to the present invention it is possible, by making use of the horizontal motion of the movable support means 6 and the vertical motion of the bridge 4, that a filter 11 having been used in the most recent measuring cycle is stripped off from the suction pipe 10 and is substituted for by a new filter 24 to be used in the next measuring cycle. However, in this embodiment it is necessary in the course of the next following measuring cycle to position a further, new filter 24 in the recess 26 of the cover 25.

In contrast thereto the second embodiment shown in FIGS. 4 and 5, which will be described now, permits a multiple filter exchange, without the interference of a service person upon every measuring cycle.

Figure 4:
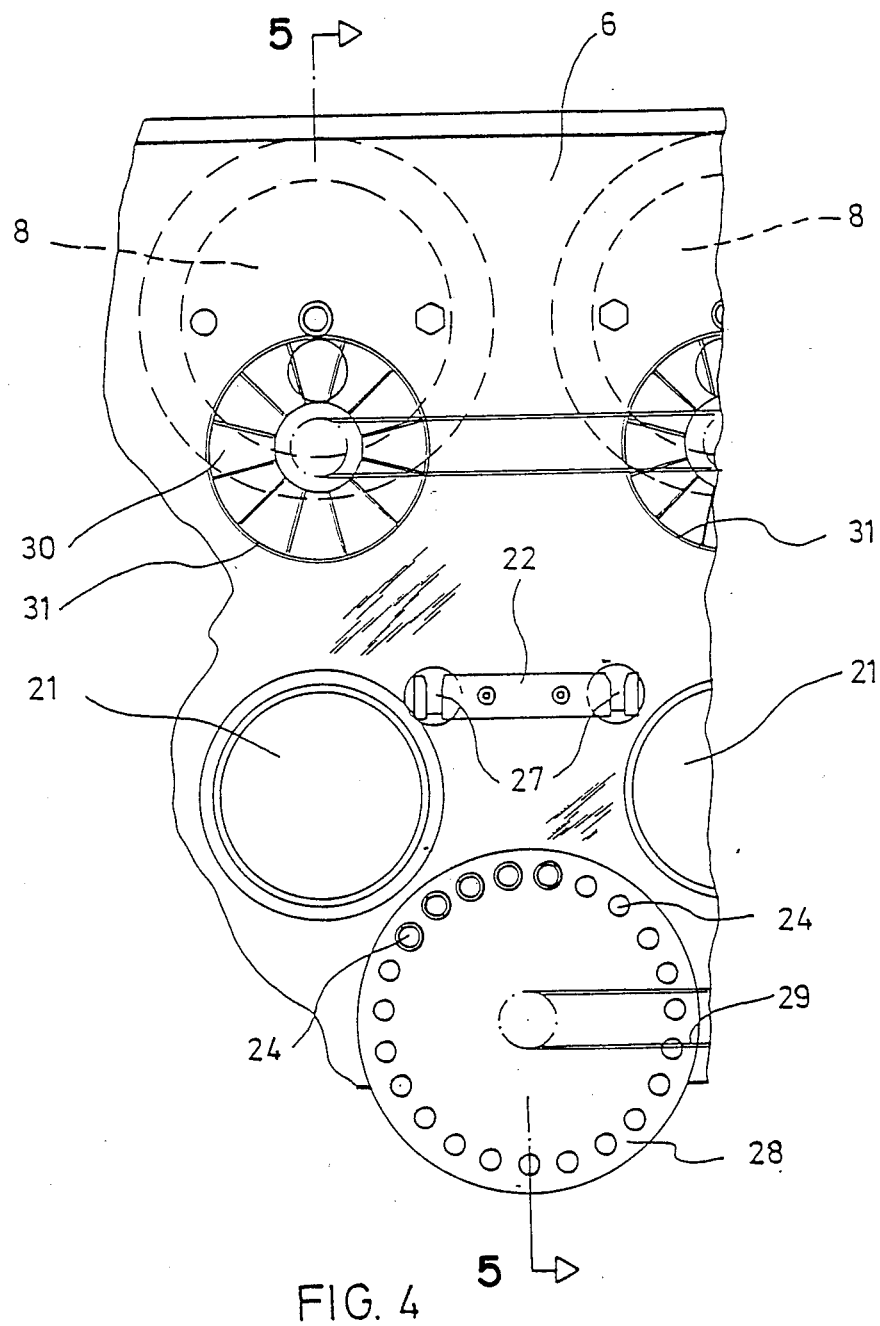
FIG. 4 is a top view of a section of a second completely automated embodiment of the dissolution testing apparatus.

FIG. 4 shows a top view of a section of the second embodiment of the dissolution testing apparatus. In this drawing, as well as in FIG. 5, again reference numerals used with indication to the first embodiment are used for identification of similar or equal parts. As can be seen from the top view, a filter stripping means 22 with two fork-shaped recesses 27 into which two suction pipes 10 can be slid is arranged between two rinsing vessels 21. The two rinsing vessels 21 shown here, out of a plurality of rinsing vessels, one arranged beside the next and the two measuring vessels 8 out of a plurality of measuring vessels, one arranged beside the next, each are disposed one beside the other perpendicularly to the direction of motion of the movable support means 6. In the middle, between two respective rinsing vessels 21, is positioned a rotary disk 28 provided with a plurality of filters 24 being arranged on the disk at even angular distances. The rotary disk 28 together with further disks (not shown) is commonly driven via a driving connection 29 by a driving means in the form of a stepping motor.

Figure 5:
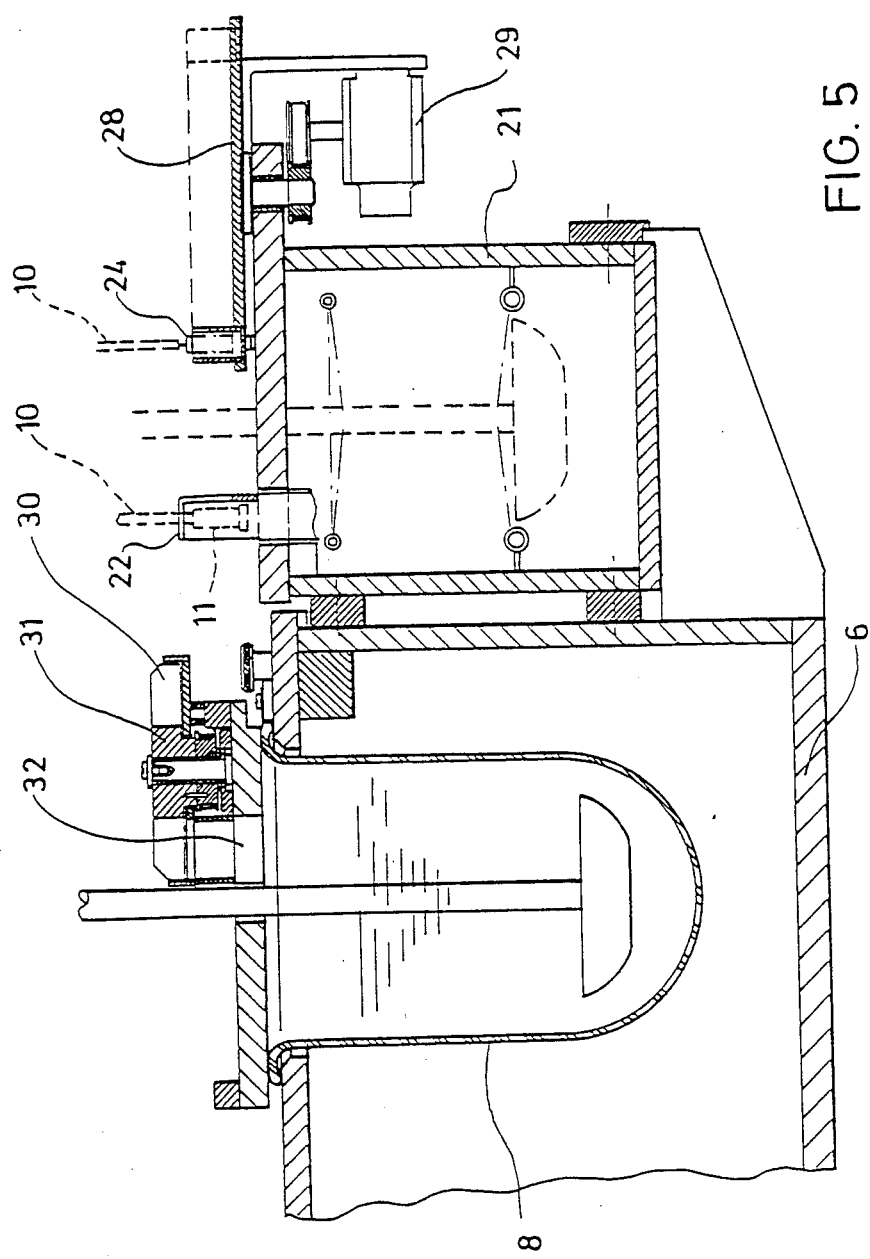
FIG. 5 is a sectional view of the second embodiment shown in FIG. 4 along the line V—V.

As can be seen in particular from the cross-sectional view of FIG. 5, the movable support means 6 at first is moved into the first position in which it assumes a relative position with respect to the suction pipes 10, such position being indicated by the dotted representation of the suction pipes 10. In this position a vertical movement of the bridge 4 and thus of the suction pipes 10 is sufficient for stripping off the filter 11. Subsequently, the movable support means 6 is driven into the second position relative to the suction pipes 10, such position being indicated by the full-line representation of the suction pipes 10 in FIG. 5. New filters 24 are slid over the suction pipes 10 by lowering the suction pipes 10 with respect to the rotary disk 28.

In the course of the subsequent measuring cycle the rotary disk is moved further by such an angle of rotation that the new filter 24 comes into the position, as shown in FIG. 5.

As can be seen from FIGS. 4 and 5, a conveyor means 31 comprising sector-shaped receptions 30 for the medical tablets to be examined as to their dissolution behaviour are arranged above the measuring vessels 8, which conveyor means can be driven stepwise in a rotary direction. When a sector-shaped reception 30 is moved past the orifice 32 in the bottom of the conveyor means 31, the medical tablet to be examined drops into the measuring vessel 8 filled with liquid. By this measurement a starting of the dissolution test, being accurately fixed with respect to time, can be adjusted.

In variation to the rotary-disk-shaped means shown in FIGS. 4 and 5 for receiving new filters and for transferring the new filters into a position in which they can be slid over the suction pipes, it is also possible to use a linear reception for filters, moving the filters in a linear direction into position in which they can be slid over the suction pipes.

When using filter stripping means angularly inclined with respect to the horizontal line, the stripping off of the filters 11 can be effected alone by the horizontal movement of the movable support means 6, without a lifting of the suction pipes with respect to the movable support means becoming necessary for stripping off.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed:

1. A dissolution testing apparatus comprising in combination
   a rinsing stand comprising at least one rotatable rinsing paddle capable of being lifted and lowered in a vertical direction relative to a measuring vessel,
   a test stand comprising at least one rotatable test stand mixing paddle capable of being lifted and lowered in a vertical direction relative to a measuring vessel,
   a movable support means including at least one measuring vessel, wherein by means of lowering said test stand mixing paddle, a liquid containing a substance to be examined with respect to its dissolution behaviour can be stirred, said support means being movable between said rinsing stand and said test stand during a lifted position of said test stand paddle and said rinsing paddle, and shiftable with respect to said rinsing stand and said test stand, a suction pipe including a filter by means of which the liquid containing the substance to be examined is extractable when said support means is in the position of said test stand, said suction pipe being lifted and lowered together with the lifting and lowering of said test stand mixing paddle relative to the measuring vessel, and a filter stripping means mounted on said movable support means by means of which said filter can be engaged by said filter stripping means in a first defined position of said movable support means.

2. The dissolution testing apparatus as in claim 1, wherein
said filter stripping means is disposed such that upon movement of said movable support means across a part of its path from said test stand to said rinsing stand into a first position said filter can be engaged by said filter stripping means and
during subsequent lifting of said suction pipe said filter can be stripped off from said suction pipe.

3. The dissolution testing apparatus as in claim 2, wherein
a filter loading means is positioned on movable support means, provided with a new filter such that when said suction pipe is lowered into a second position upon movement of said support means, in said lowered position said suction pipe is connectable to a new filter by means of a clamp fit.

4. The dissolution testing apparatus as in claim 3, wherein
said filter loading means comprises a rotary disk on which a plurality of new filters are arranged at uniform angular distances, and
said rotary disk is turnable by said angular distance upon each deposition of a new filter on said suction pipe by a driving means.

5. The dissolution testing apparatus as in claim 4, wherein said
driving means is a stepping motor.

6. The dissolution testing apparatus as in claim 4, wherein
at least two measuring vessels, two test stand paddles, two rinsing paddles and two suction pipes are provided each one beside the other in a direction perpendicular to the direction of motion of said movable support means, and
said rotary disk serves as a common filter loading means for two adjacent suction pipes arranged such that the lowered suction pipes in the second position of the movable support means engages with two new filters arranged on said common rotary disk.

7. A dissolution testing apparatus as in claim 3, wherein
said movable support means includes at least one rinsing vessel into which said at least one rinsing paddle can be submerged in the first position of said movable support means.

8. The dissolution testing apparatus as in claim 1, further including a filter loading means positioned on said movable support means, provided with a new filter such that when said suction pipe is lowered into a second position upon movement of said support means, in said lowered position said suction pipe is connectable to a new filter by means of a clamp fit.

9. The dissolution testing apparatus as in claim 8, wherein
said filter loading means comprises a rotary disk on which a plurality of new filters are arranged at uniform angular distances, and
said rotary disk is turnable by said angular distance upon each deposition of a new filter on said suction pipe by a driving means.

10. The dissolution testing apparatus as in claim 9, wherein said
driving means is a stepping motor.

11. The dissolution testing apparatus as in claim 9, wherein
at least two measuring vessels, two test stand paddles, two rinsing paddles and two suction pipes are provided each one beside the other in a direction perpendicular to the direction of motion of said movable support means, and
said rotary disk serves as a common filter loading means for two adjacent suction pipes arranged such that the lowered suction pipes in the second position of the movable support means engages with two new filters arranged on said common rotary disk.

12. A dissolution testing apparatus as in claim 8, wherein
said movable support means includes at least one rinsing vessel into which said at least one rinsing paddle can be submerged in the first position of said movable support means.

13. A dissolution testing apparatus as in claim 1, wherein said rinsing paddles, said test mixing paddles and said suction pipes are connected to a bridge liftable and lowerable vertically relative to said support means.

* * * * *